United States Patent [19]

Bacus

[11] Patent Number: 5,086,476
[45] Date of Patent: Feb. 4, 1992

[54] METHOD AND APPARATUS FOR DETERMINING A PROLIFERATION INDEX OF A CELL SAMPLE

[75] Inventor: James W. Bacus, Hinsdale, Ill.

[73] Assignee: Cell Analysis Systems, Inc., Lombard, Ill.

[21] Appl. No.: 315,289

[22] Filed: Feb. 24, 1989

Related U.S. Application Data

[63] Continuation-in-part of Ser. No. 121,674, Nov. 17, 1987, Pat. No. 5,016,283, and a continuation-in-part of Ser. No. 106,717, Oct. 6, 1987, Pat. No. 5,008,185, and a continuation-in-part of Ser. No. 927,285, Nov. 4, 1986, Pat. No. 5,018,209, which is a continuation-in-part of Ser. No. 794,937, Nov. 4, 1985, Pat. No. 4,741,043, said Ser. No. 121,674, is a continuation-in-part of Ser. No. 927,285.

[51] Int. Cl.$^5$ .............................................. G06K 9/00
[52] U.S. Cl. .................................. 382/6; 364/413.08; 356/39
[58] Field of Search .................... 382/6, 1, 8; 364/413.08, 413.07, 313.09, 413.1; 356/39, 40, 432, 410; 128/665, 633, 653 R, 653 A; 358/101; 250/237 R

[56] References Cited

U.S. PATENT DOCUMENTS 3,297,879  1/1963  Meyer ................................ 250/237
3,481,659  12/1969  Rosenberg ............................ 350/94

(List continued on next page.)

FOREIGN PATENT DOCUMENTS 59-88716  5/1984  Japan .

OTHER PUBLICATIONS

King and Green, "Monoclonal Antibodies Localize Oestrogen Receptor in the Nuclei of Target Cells", *Nature* 307:745–747, 1984.
Jensen et al., "Receptors Reconsidered: A 20–Year Perspective", *Recent Progress in Hormone Research* 38:1–39.
Greene et al., "Monoclonal Antibodies to Human Estrogen Receptor", *Proc. Natl. Acad. Sci. U.S.A* 77:5115–5119, 1980.
James and Goldstein, "Haemoglobin Content of Individual Erythrocytes in Normal and Abnormal Blood", *British Journal of Haemotology* 28:89–102, 1974.
McCarty et al., "Estrogen Receptor Analyses", *Arch Pathol Lab Med* 109:716–721, 1985.
"Immunocytochemical Assay for the Detection of Human Estrogen Receptor", Abbott Laboratories, 83-1547/R2, 1986.
Sherrod and Taylor, "Nonlymphocyte Tumor Markers in Tissues", *Immunopathology and Immunohistology*, Chap. 145, pp. 938–947.
King et al., "Comparison of Immunocytochemical and Steroid-binding Assays for Estrogen Receptor in Human Breast Tumors", *Cancer Research* 45:293–294, 1982.
Thorell, B., "Cell Studies with Microspectrography", pp. 95–119.

*Primary Examiner*—Michael Razavi
*Attorney, Agent, or Firm*—Fitch, Even, Tabin & Flannery

[57] ABSTRACT

An image processing method and apparatus determines a proliferation index of a cell sample by staining the cells with a chromogen for a proliferation substance and a counterstain for the cell nuclei. The chromogen is activated by an antibody-enzyme conjugate which binds to the proliferation substance to produce a stained cell sample. The stained cell sample is examined with an optical microscope, forming a portion of the apparatus, which produces a magnified cell sample image. The apparatus optically filters the cell sample image and produces a pair of optically enhanced proliferation substance and cell nuclei images. The enhanced images are electronically analyzed to determine the amounts of cell nuclei and proliferation substance appearing in the images, respectively. The amounts are then compared to yield a proliferation index for the portion of the cell sample appearing in the cell sample image.

7 Claims, 10 Drawing Sheets

U.S. PATENT DOCUMENTS

| | | | |
|---|---|---|---|
| 3,532,412 | 10/1970 | Miller | 350/95 |
| 3,773,425 | 11/1973 | Bentley | 356/191 |
| 3,847,486 | 11/1974 | McCabe | 356/205 |
| 3,851,156 | 11/1974 | Green | 235/151.3 |
| 3,895,854 | 7/1975 | Ziffer | 350/20 |
| 3,907,437 | 9/1975 | Hirschfeld | 356/39 |
| 3,977,791 | 8/1976 | Weber et al. | 356/168 |
| 4,000,417 | 12/1976 | Adkisson et al. | 356/39 |
| 4,017,192 | 4/1977 | Rosenthal | 356/39 |
| 4,045,772 | 8/1977 | Bouton et al. | 340/146.3 |
| 4,048,616 | 9/1977 | Hart et al. | 340/146.3 |
| 4,061,914 | 12/1977 | Green | 250/201 |
| 4,097,845 | 6/1978 | Bacus | 340/146.3 |
| 4,125,828 | 11/1978 | Resnick et al. | 340/146.3 |
| 4,129,854 | 12/1978 | Suzuki et al. | 340/146.3 |
| 4,132,767 | 1/1979 | Tohmatsu et al. | 424/1 |
| 4,152,410 | 5/1979 | Ishii | 424/1 |
| 4,160,817 | 7/1979 | Bucovaz et al. | 424/1 |
| 4,174,178 | 11/1979 | Ouchi et al. | 356/39 |
| 4,175,860 | 11/1979 | Bacus | 356/39 |
| 4,199,748 | 4/1980 | Bacus | 340/146.3 |
| 4,207,554 | 6/1980 | Resnick et al. | 340/146.3 |
| 4,213,036 | 7/1980 | Kopp et al. | 235/92 |
| 4,219,440 | 8/1980 | Runck et al. | 252/408 |
| 4,227,814 | 10/1980 | Soodak et al. | 356/410 |
| 4,231,660 | 11/1980 | Remy et al. | 356/244 |
| 4,232,001 | 11/1980 | Jensen et al. | 424/1 |
| 4,232,970 | 11/1980 | Sawamura et al. | 356/432 |
| 4,257,709 | 3/1981 | Mostyn, Jr. | 356/435 |
| 4,307,376 | 12/1981 | Miller et al. | 340/146 |
| 4,362,386 | 12/1982 | Matshushita et al. | 356/39 |
| 4,389,669 | 6/1983 | Epstein et al. | 358/101 |
| 4,404,683 | 9/1983 | Kobayashi et al. | 382/6 |
| 4,408,231 | 10/1983 | Bushaw et al. | 358/280 |
| 4,446,871 | 5/1984 | Imura | 128/633 |
| 4,453,266 | 6/1984 | Bacus | 382/6 |
| 4,513,438 | 4/1985 | Graham et al. | 382/6 |
| 4,523,278 | 6/1985 | Reinhardt et al. | 364/413 |
| 4,562,593 | 12/1985 | Ooe et al. | 382/6 |
| 4,592,089 | 5/1986 | Hartman | 382/6 |
| 4,741,043 | 4/1988 | Bacus | 382/6 |

ORIGINAL IMAGE
SEEN THOUGH
WHITE LIGHT

||||  GREEN

≡  BROWN

▦  GREEN AND BROWN

620 NM (RED)
NARROW BANDPASS
FILTERED IMAGE

///  GREY SCALE OR
     OPTICAL DENSITY

500 NM (GREEN)
NARROW BANDPASS
FILTERED IMAGE

///  GREY SCALE OR
     OPTICAL DENSITY

```
QUANTITATIVE PROLIFERATION INDEX          DATE: 17/DC/88  TIME: 13:30:18
TISSUE SECTION SCREEN

PATIENT IDENTIFICATION                              LABEL
ACCESSION NUMBER                                    SET LIGHT
COMMENT                                             CHECK LIGHT
                                                    BACKGROUND LIGHT
    LIGHT LEVEL  0                                  SET XY
                                                    CURRENT XY
                                                    DISPLAY XY

TOTAL FIELD COUNT      0                        NUCLEAR THRESHOLD
    TOTAL PROLIFERATION INDEX    .0      %          ANTIBODY THRESHOLD
    TOTAL NUCLEAR AREA           0  um²             DISPLAY NUC-ANTI MASK
                                                    WINDOW

CURRENT PROLIFERATION INDEX  .0      %          MEASURE
    CURRENT NUCLEAR AREA         0  um²             MERGE DATA

CLEAR DATA
                                                    DISAPPEAR
                                                    HELP    EXIT
```

FIG. II

QUANTITATIVE PROLIFERATION INDEX           DATE: 17/DC/88 TIME: 15:27:57
CELL PREPARATION SCREEN

PATIENT IDENTIFICATION                                         LABEL
ACCESSION NUMBER                                               SET LIGHT
COMMENT                                                        CHECK LIGHT
                                                               BACKGROUND LIGHT
LIGHT LEVEL    0                                               SET XY
                                                               CURRENT XY
                                                               DISPLAY XY

| TOTAL FIELD COUNT        | 0   |   |
|--------------------------|-----|---|
| TOTAL PROLIFERATION INDEX| .0  | %|
| TOTAL NUCLEAR COUNT      | 0   |   |

NUCLEAR THRESHOLD
                                                               ANTIBODY THRESHOLD
CURRENT PROLIFERATION INDEX    .0  %                           DISPLAY NUC-ANTI MASK
CURRENT NUCLEAR COUNT           0                              WINDOW
                                                               ANTI/NUC THRESHOLD (%)
ANTIBODY PER NUCLEAR THESHOLD  2.0 %                           MEASURE
                                                               MERGE DATA

CLEAR DATA
                                                               DISAPPEAR
                                                               HELP    EXIT

FIG.12

METHOD AND APPARATUS FOR DETERMINING A PROLIFERATION INDEX OF A CELL SAMPLE

CROSS REFERENCES TO RELATED APPLICATIONS

This is a continuation-in-part of copending U.S. application Ser. No. 121,674, filed Nov. 7, 1987 and now U.S. Pat. No. 5.016,283 in the names of James W. Bacus and Robert J. Marder for Methods and Apparatus for Immunoploidy Analysis; a continuation-in-part of copending U.S. application Ser. No. 106,717, filed Oct. 6, 1987 and now U.S. pat. No. 5,008,185 in the name of James W. Bacus for Methods and Apparatus for the Quantitation of Nuclear Protein; and a continuation-in-part of copending U.S. application Ser. No. 927,285, filed Nov. 4, 1986 and now U.S. pat. No. 5,018,209 in the name of James W. Bacus for Analysis Method and Apparatus for Biological Specimens.

U.S. application Ser. No. 121,674, filed Nov. 17, 1987, in turn, is a continuation-in-part of U.S. application Ser. No. 927,285, filed Nov. 4, 1986 in the name of James W. Bacus for Analysis Method and Apparatus for Biological Specimens; which is a continuation-in-part of U.S. application Ser. No. 794,937, filed Nov. 4, 1985 in the name of James W. Bacus for Method of and an Apparatus for Image Analyses of Biological Specimens, now U.S. Pat. No. 4,741,043; all of which are commonly assigned. The disclosures of each of the aforementioned applications are hereby expressly incorporated herein by reference.

This is related to an application for Dual Color Camera Microscope and Methodology For Cell Staining And Analysis to James W. Bacus filed on the date of filing of this application.

BACKGROUND OF THE INVENTION

The invention relates to a system for performing a assay of a cell sample to provide an accurate quantitative analysis of a characteristic of the cells which have been sampled. More particularly, the invention is directed to a system which receives images of stained cells and enhances the cell images prior to further processing to determine the proliferation index of the enhanced cell images.

One of the problems which faces pathologists in their clinical practice is that of determining whether a cell sample taken from a patient during a biopsy procedure or the like is benign or malignant. Although a surgeon may have a good intuition about the type of tissue mass which he has removed, nevertheless he must confirm his preliminary diagnosis with a histological examination of the cell sample removed from the patient. The histological examination entails cell staining procedures which allow the morphological features of the cells to be seen relatively easily in a light microscope. A pathologist after having examined the stained cell sample, makes a qualitative determination of the state of the tissue or the patient from whom the sample was removed and reaches a conclusion as to whether the patient is normal or has a premalignant condition which might place him at risk of a malignancy in the future or has cancer. While this diagnostic method has provided some degree of predictability in the past, it is somewhat lacking in scientific rigor since it is heavily reliant on the subjective judgement of the pathologist.

Attempts have been made to automate the cellular examination process. In U.S. Pat. No. 4,741,043 to Bacus for Method and Apparatus for Image Analyses of Biological Specimens, an automated method and a system for measuring the DNA of cells are disclosed which employ differential staining of the DNA in cell nuclei with a Feulgen Azure A stain and image processing. While the system provides an accurate assay of the cellular DNA its predictive power for cell replication, a key indicator of the presence of cancer, could be improved.

It is well known that cells follow a replication cycle; for a further discussion of the cycle reference may be made to Pages 330–336 of McGraw-Hill Encyclopedia of Science and Technology, 6th Edition, 1987. Most somatic cells of an adult human replicate at a relatively slow rate, only rapidly enough to replace cells shed by the body and lost to normal cellular wear and tear. At any instant, most of those somatic cells are in the GO- or resting phase of the replication cycle. When they leave the resting phase they enter the GI or first gap phase but are not yet producing extra DNA. Upon becoming committed to the S-phase, however, they do produce other material such as proliferation substances e.g. cyclin and other S-phase proteins. The cells in the synthesis or S-phase are actively synthesizing DNA and produce double the amount of DNA normally contained in the cell nuclei in preparation for mitosis or division of the cell nuclei during cell replication. A normal human somatic cell contains 23 chromosome pairs and is in the diploid state. The diploid state is also referred to as the 2N state. At the time of replication the number of chromosome pairs increases to 46, double the normal amount in antic of cell division. The chromosome state immediately before replication is referred to as the 4N state. The cells then enter the second gap phase or G2 phase in which little or no DNA is synthesized. Following the G2 phase is the mitosis or M-phase in which the cells themselves divide. If the cells are actively proliferating they may reenter the G1 phase.

Although DNA analysis may be adequate for estimating the number or proportion of proliferating cells in normal cells or tissue, it should be appreciated that this is not the case with malignant cells, the very ones for which it often is important to know the extent of proliferation. This is because malignant cells often have increased amounts of DNA, even in the G0 phase, due to increased chromosome content, and often increased of chomosomes. Therefore, it is impossible to conclude with certainty from a DNA analysis that a particular cell, e.g. one having 1.5 times the normal DNA content, is a malignant cell with additional chromosomes, or chromosome parts, or is a normal cell which is halfway through the S-phase having only replicated one-half the DNA necessary for cell division. Thus it is clear that an analysis method independent of DNA, utilizing other markers, such as variously produced proteins associated with S-phase proliferation and the cell division process, has many advantages It should also be appreciated that quantitating on a cellular proliferation index has previously been performed by counting the numbers of cells in a cell sample carrying an indicator or stain for a proliferation substance. For instance, a well known method of determining the proliferation index is to stain the cells with an immunofluorescent dye which binds to cyclin and manually count the fluorescent and non-fluorescent stained cells to determine the proportion of cells having proliferation substance.

Another method of determining the proliferation index of cells is the grain counting method; for a further discussion of this grain counting method reference may be made to Pages 107-112 of The American Journal of Pathology, Volume 134, No. 1, January, 1989. In that method, tritiated thymidine is added to a cell culture growth medium. Proliferating cells take up the tritiated thymidine and incorporate it into DNA being synthesized in the cells. The cells are then fixed and placed in proximity with a photographic emulsion. Decay products of the tritium expose portions of the emulsion. The exposed portions may be visualized as grains by photographic development processes. Cells with overlying grains and with non-overlapping grains, are then counted to determine the proliferation index. One of the drawbacks of this method lies in the fact that it is very time consuming. It is necessary that the cells be harvested alive and kept alive long enough to take up the tritiated thymidine. The cells must then be fixed and held in proximity with the emulsion in order to expose it. Since relatively low intensities of radiation may emanate from the cells, it may take days or even weeks to obtain a latent image on the emulsion, which must then be developed. In the meantime, the patient's disease may be progressing.

One of the drawbacks of the prior art methods is that they are prone to human error due to the tedium of counting the cells on a microscope slide under high magnification. Often the people examining the slides only are able to estimate the relative number of cells which show a positive result for proliferation substance.

The prior imaging systems have also suffered from the problem that while they usually accurately identify the images of cell objects in an image being processed they do not always accurately identify boundaries of the cell objects being evaluated. This may be a problem when an assay is being performed on the cell objects on the basis of their image areas.

The prior art methods of quantitatively analyzing the cell samples for proliferation substances could not be automated simply. This is because it is necessary to determine a baseline value for the total number of cells examined as opposed to the number of cells which have proliferation substance. In order to make this type of evaluation an automatic system must be able to recognize what constitutes a cell or a cell nucleus. In order to solve this baseline recognition problem the instant invention employs separate stains for the cell nuclei and the proliferation substances. In addition, the stains are separated spectrally so that they can be readily distinguished by optical filters which are compatible with them. The optical separation of the two components to be measured makes the subsequent analysis of the cell images more convenient to automate.

A similar difficulty is encountered in an image analysis based on cell object areas when cell objects images overlap, touch or otherwise share contiguous areas. In that case, what is actually a double or triple object image may not be tallied properly resulting in an inaccurate result or conclusion.

SUMMARY OF THE INVENTION

The present invention provides a rapid and convenient method and an apparatus for practicing the method for determining the amount of a proliferation substance in a cell sample. The cell sample may be a tissue sample or a cell preparation. Tissue samples are frozen sections or paraffin sections of connected cells. The cell preparations are made from body fluids such as cerebrospinal fluid, blood, pleural effusions and the like. Cell preparations may also be made from needle aspirates of tumors, cysts or lymph nodes. Cell preparations may also be made from touch preparations which are made by touching a freshly microtomed surface of a piece of tissue to a microscope slide to which the cells cling. In particular, the apparatus and method employ a mouse PAP based staining system with a rabbit anti-mouse bridging antibody, wherein mouse antibodies for a proliferation substance such as cyclin or the antigen for Ki-67-. are used. The PAP antibodies are complexed with an enzyme, in this embodiment horseradish peroxidase (HRP). The cells are contacted with the mouse primary antibody which binds only to portions of the cells which have epitopes identifying them as proliferation substance. After applying the bridging antibody, and the PAP antibodies, a stain, in this embodiment 3, 3' diaminobenzidine tetrahydrochloride (DAB), and hydrogen peroxide $H_2O_2$ are placed in contact with the cells having the antibody-HRP conjugate bound to their proliferation substance sites. The HRP catalyzes a chromogen forming reaction only at the areas where it is bound. The catalyzed chromogen forming reaction produces a red-brown chromogen precipitate bound to proliferation sites.

The cells are then stained with a counterstain, in this instance ethyl green, which also is commonly known as methyl green. The image of the cells is magnified in a light microscope and split into a pair of separated images. The separated images are enhanced by a pair of narrow bandpass optical filters. One of the narrow bandpass optical filters preferentially transmits light having a wavelength at the transmission peak of the counterstain thereby producing an optically enhanced proliferation substance image which only has background and the red-brown chromogen. The background of the proliferation substance image is composed of the cell nuclei, cytoplasm and the like which have substantially zero optical density. The proliferation substance sites have a relatively high optical density. Thus the only features which are easily perceivable are the proliferation substance sites.

The other narrow bandpass optical filter preferentially transmits in the regions of spectral absorption for both the red-brown stain and the counterstain. This filter produces an optically enhanced cell nuclei image of all nuclei, with and without proliferation antigen.

The inventive apparatus senses the enhanced proliferation substance image with a first monochrome television camera. The enhanced cell nuclei image is sensed by a second monochrome television camera. Analog signals representative of the images are fed to respective image processors. The image processors convert the analog signals to digitized arrays of pixels which are stored in internal frame buffers.

When a tissue section is being examined the apparatus computes an area of the proliferation substance image which has high optical density, yielding an area measure for the proliferation substance in that image field. When a cell preparation is being examined the apparatus computes the proliferation index on the basis of the percentage of cell nuclei having more than a threshold amount of proliferation substance therein.

BRIEF DESCRIPTION OF THE DRAWINGS

FIG. 11 is a screen display of the tissue screen;

FIG. 12 is a screen display of the cell preparation screen.

DETAILED DESCRIPTION OF THE PREFERRED EMBODIMENT

Figure 1:
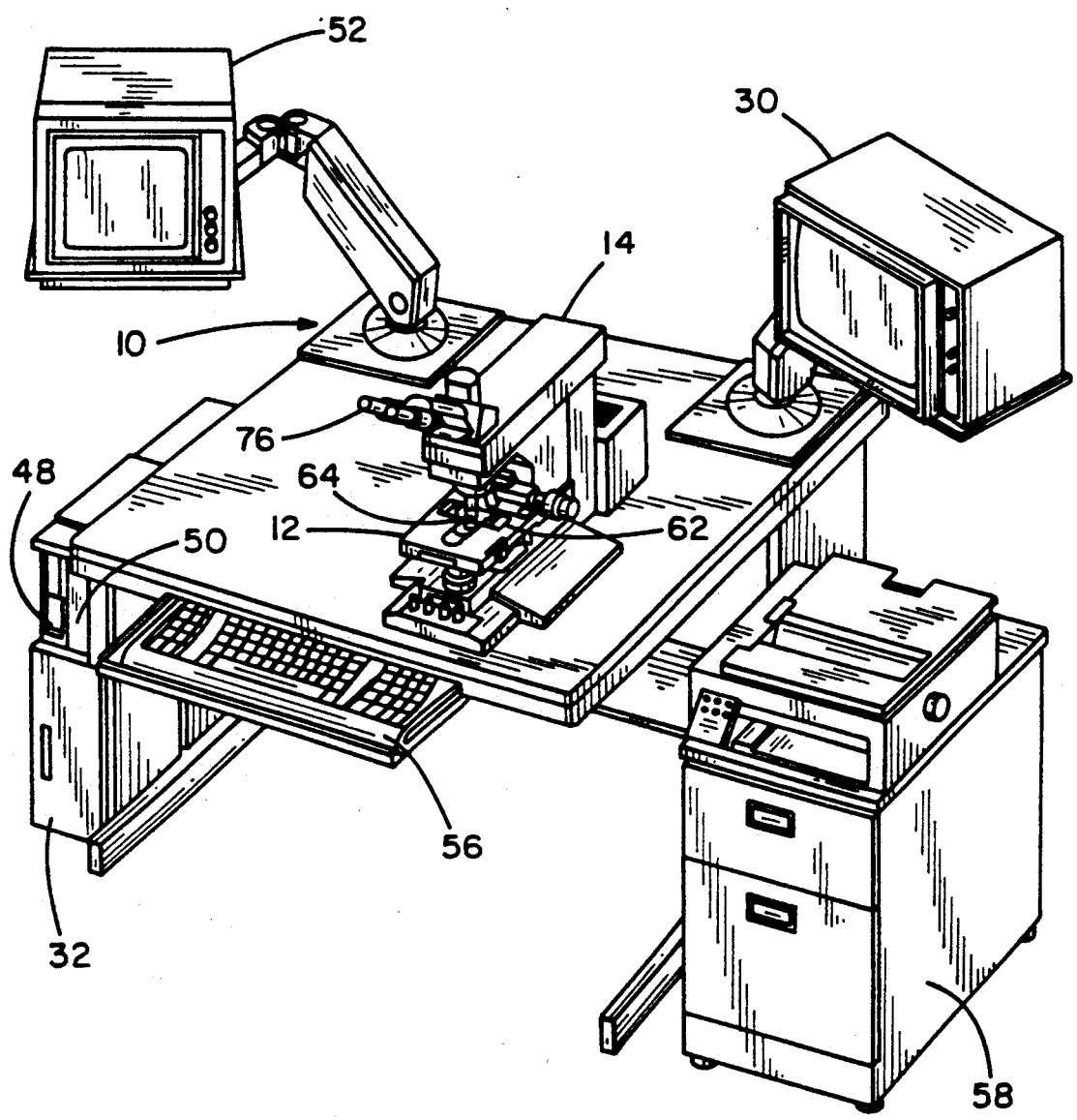
FIG. 1 is an isometric view of an apparatus for determining a proliferation index of a cell sample embodying the present invention.
Figure 2:
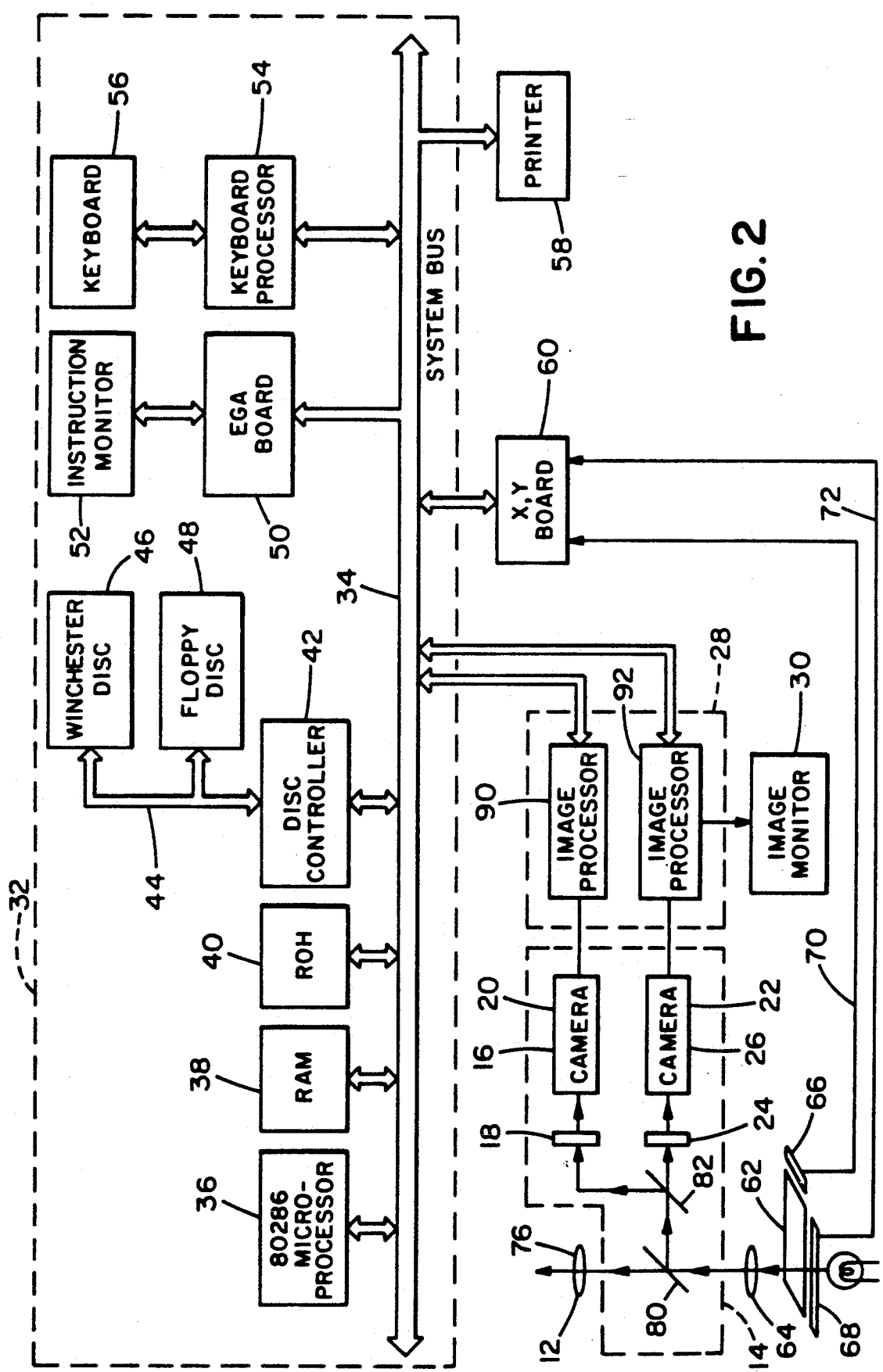
FIG. 2 is a block diagram of the apparatus of FIG. 1.
Figure 3:
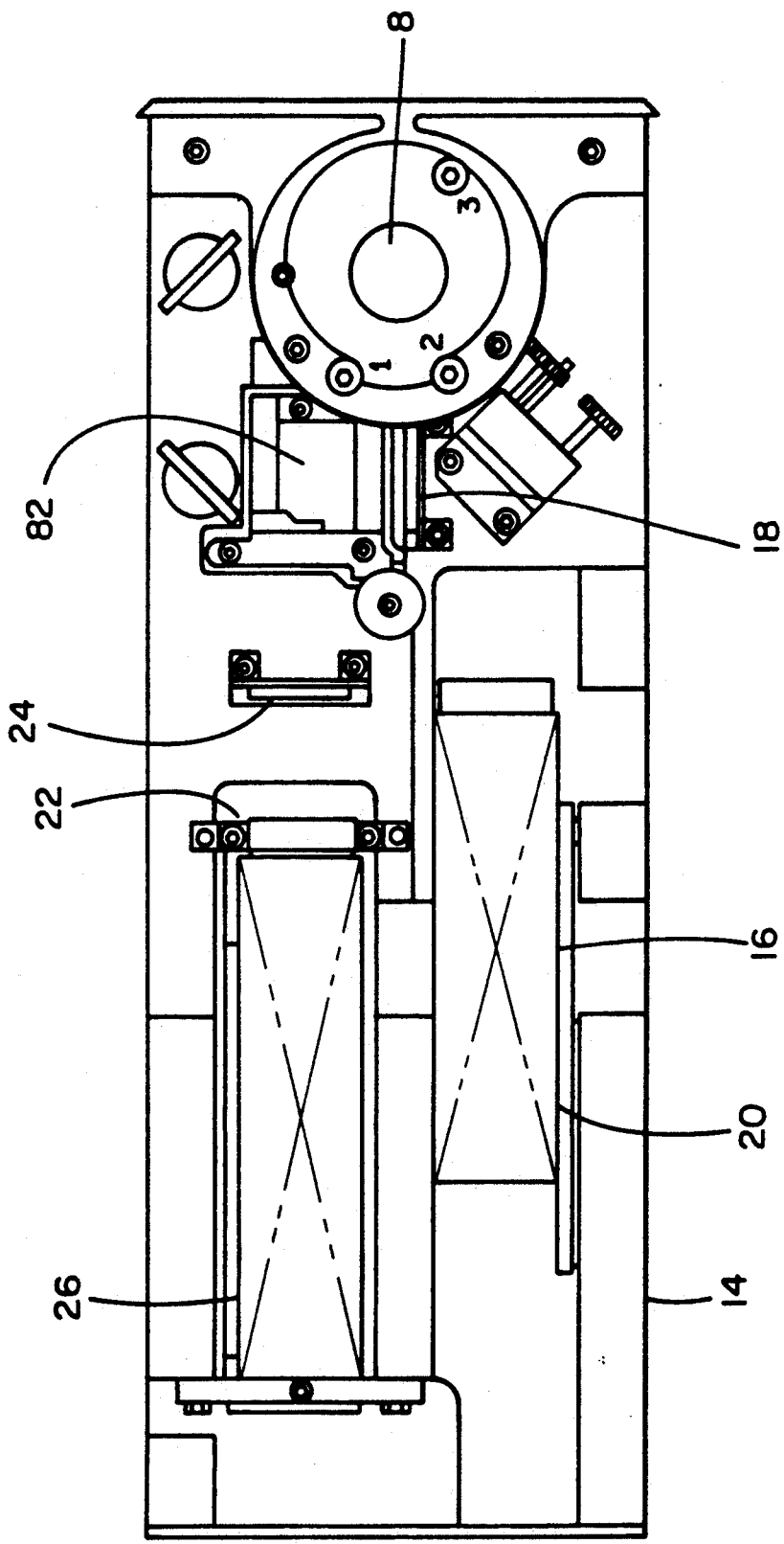
FIG. 3 is an elevational view of an optical conversion module of the apparatus of FIG. 1.

Referring now to the drawings and especially to FIG. 1, an apparatus embodying the present invention and generally identified by numeral 10 is shown therein. The apparatus 10 comprises an optical microscope 12, which may be of any conventional type but in this embodiment is a Reichart Diastar or Microstar. An optical conversion module 14 is mounted on the microscope 12 to enhance optically a magnified image of a cell sample viewed with the microscope 12. The optical conversion module 14, as may best be seen in FIG. 3, has a cell nuclei sensing means comprising a cell nuclei image optical enhancement unit 16. The cell nuclei image optical enhancement unit 16 has a $620\pm20$ nanometer red narrow bandpass optical transmission filter 18 and a television camera 20 for receiving a filtered image from the filter 18. A proliferation substance sensing means comprising a proliferation substance optical enhancement module 22 has a green $500\pm20$ nanometer narrow bandpass optical transmission filter 24 and a television camera 26 and is also part of the optical conversion module 14. Each of the television cameras 20 and 26 generates a standard NTSC compatible signal representative, respectively, of an enhanced cell nuclei image and an enhanced proliferation substance image. An image processing system 28 is connected to the television cameras 20 and 26 to receive the enhanced cell nuclei image signal and the enhanced proliferation substance image signal and to store a cell nuclei pixel array and a proliferation substance pixel array therein. The image processor 28 is connected to a computer 32, in the present embodiment, an IBM personal computer model AT for processing of the cell nuclei and proliferation substance pixel arrays.

The computer 32 includes a system bus 34, connected to the image processor unit 28. An 80286 microprocessor 36 is connected to the system bus 34. A random access memory 38 and a read only memory 40 are also connected to the system bus 34 for storage of information. A disk controller 40 is connected by a local bus 44 to a Winchester disk drive 46 and to a floppy disk drive 48 for secondary information storage. A video conversion board 50 in this embodiment, an EGA board having 256K bytes of memory, is connected to the system bus 34 to control an instruction monitor 52 connected to the EGA board 50. A keyboard processor 54 is connected to the system bus 34 to interpret signals from a keyboard 56 which is connected to the keyboard processor 54. A printer 58 is connected to the system bus 54 for communication therewith. An X Y or image field board 60 is connected to the system bus 34. The X Y board 60 also is connected to a slide holder of the microscope 12 to sense the relative position of a slide 62 with respect to a microscope objective 64 and thus identify a field being viewed. Included is a Y position sensor 66 and an X position sensor 68. The Y position sensor 66 is connected via a communication path 70 to the X Y board 60. The X position sensor 68 is connected via a communication path 72 to the X Y board 60. The microscope 12 also includes an eyepiece 76 in optical alignment with the objective 74 for magnification of light forming an image of a cell sample on the slide 62.

The method of the instant invention is practiced by collecting a cell sample, which may be in the form of a tissue section made from a frozen section or a paraffinized section and having both cell nuclei, cell fragments and whole cells therein. Alternatively, the cell sample may be a cell preparation of the type which might be taken from blood, pleural effusions, cerebrospinal fluid, or by aspirating the contents of a cyst or a tumor. The cells of the cell sample are placed on the slide 62 and fixed thereon. A monoclonal antibody for a proliferation substance to be detected in the cells is then placed in contact with them. The monoclonal antibody may for instance be Ki-67 or may be an antibody for 5-bromodeoxyuridine, for cyclin or for other proteins which indicate that cellular replication is occurring. The monoclonal antibody selectively binds to all points on and within the cells where the proliferation substance is present. The monoclonal antibody also has bound thereto a bridging antibody and a peroxidase anti-peroxidase complex. The anti-peroxidase comprises an antibody which specifically binds to the enzyme peroxidase. The peroxidase enzyme is bound to the antibody and held through the chain of antibodies to the proliferation substance in the cells.

In order to view the sites, a quantity of a mixture containing hydrogen peroxide and 3, 3' diaminobenzidine tetrahydrochloride (DAB) is applied to the cell sample on the slide. The hydrogen peroxide and the DAB react to form a chromogen consisting of a reddish-brown precipitate. The usual rate of reaction however is relatively low. The peroxidase catalyzes the chromogen-forming reaction only at the points where the peroxidase is localized. Thus, chromogen is precipitated only at the points in the cells where proliferation substance is present and the cells are preferentially stained only at the points where they have proliferation substance. After a period of about 15 minutes, the unreacted DAB and hydrogen peroxide are removed from the cell sample. The cells are then counterstained with methyl green (more properly known as ethyl green) which preferentially binds with the cell nuclei. Thus, cell nuclei are stained and the points within the cell nuclei having proliferation substance are stained reddish-brown.

The microscope slide 62 is then placed on a carrying stage of the microscope 12 and the objective 64 is focused thereon. Light from the objective 64 travels through the eyepiece 12 where at may be viewed by an observer. In addition, the optical converter module 14 includes a beam-splitting mirror 80 which carries off approximately 90% of the light to other portions of the converter. The light is fed to a dual prism dichroic mirror 82 which reflects a portion of the light to the red filter 18. The remaining portion of the light is filtered by the dichroic mirror 82 and fed to the green filter 24. The dichroic mirror 82 selectively passes light having wavelengths greater than 500 nanometers to the filter 18 20. and having a wavelength of less than 500 nanometers to the filter 24. Thus, the dichroic mirror 82 acts as a first color filter before the light reaches the color filters 18 and 24.

Figure 7:
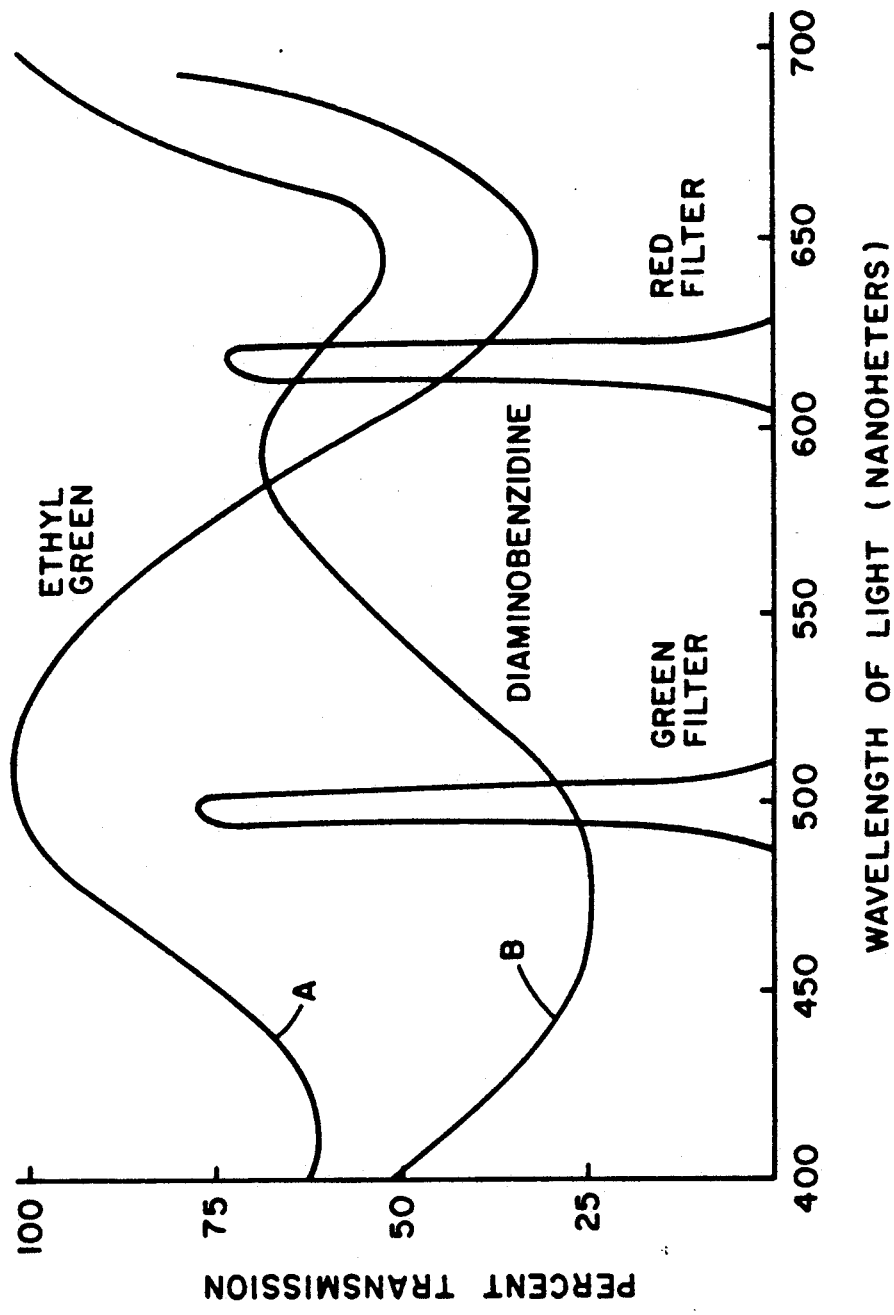
FIG. 7 is a graph of the spectral response of a chromogen, a counterstain and the narrow band optical filters.

When the light passes through the filter 18, the filter 18 preferentially blocks light from the green stained cell nuclei and provides a high contrast cell nuclei image to the camera 20. The optical characteristics of the methyl green and the DAB as well as the optical filters 18 and 24 are shown in the graph of FIG. 7. The camera 20 then generates an NTSC cell nuclei image signal which is fed to the image processor module 28. The image processor module 28 has an image processor 90 and an image processor 92. Each of the image processors 90 and 92 is a model AT428 from the Datacube Corporation. Similarly, the green filter 24, filter, provides a high contrast proliferation substance image to the camera 26. The camera 6 then feeds the proliferation substance image signal to the image processor 92. Both of the image processors 90 and 92 contain analog to digital converters for converting the analog NTSC signals to digitized arrays of pixels which are then stored within internal frame buffers. The internal frame buffers may be accessed via the system bus 34 under the control of the microprocessor 36.

Figure 4:
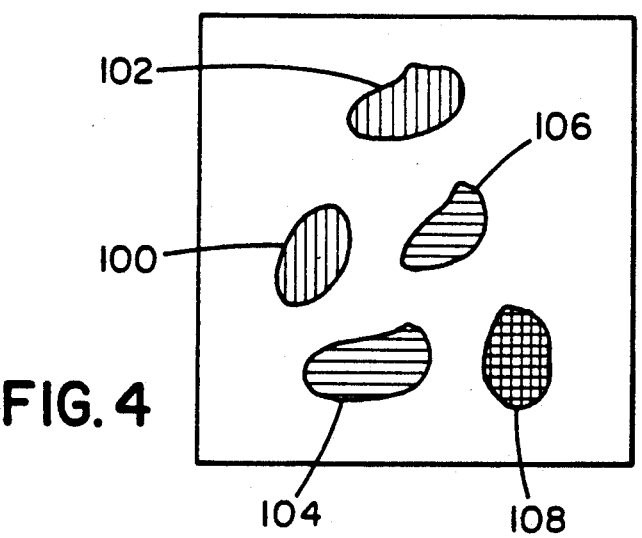
FIG. 4 is a magnified view of a stained cell sample as seen through the microscope of FIG. 1 without optical filtering.

The image of the cell sample viewed through the eyepiece 12 is of the type shown in FIG. 4 having a green cell nucleus 100, a green cell nucleus 102, a reddish-brown cell nucleus 104 having proliferation substance therein, a reddish-brown cell nucleus 106, and a reddish-brown and green cell nucleus 108. As may best be seen in FIG. 5, the cell nuclei are shown therein as they would appear through the red filter 18, which causes all of the green cell nuclei and the reddish-brown cell nuclei to darken and appear prominently. As may best be seen in FIG. 6, the proliferation substance image of the cell nuclei of FIG. 4 is shown therein with the cell nuclei 100 and 102 being rendered substantially transparent or invisible by the effect of the green filter 24. The 500 nanometer filter 24 transmits at an optical absorbing region of the DAB and transmits at an essentially one hundred percent optical transmission region of the methyl green. The 620 nanometer filter transmits at an optical absorbing region of the DAB and at an optical region of the methyl green. The cell nuclei 104, 106 and 108 having the reddish-brown chromogen deposited therein, which is an indicator for the proliferation substance, appear clearly in high contrast.

Figure 5:
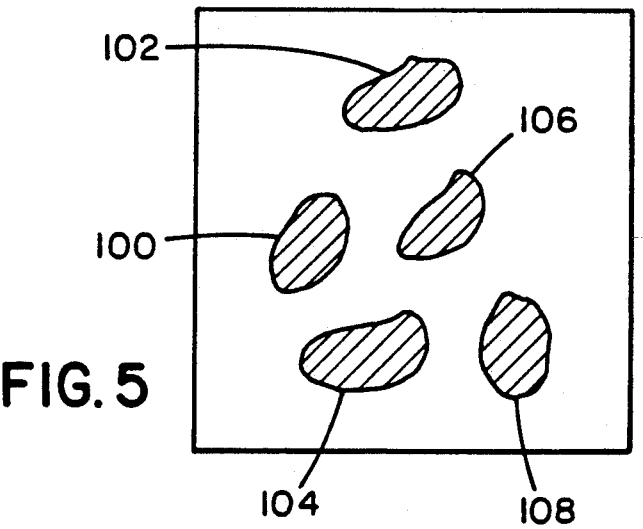
FIG. 5 is a magnified view of the stained cell sample of FIG. 4 as seen through a 620 nanometer narrow band optical filter which yields a cell nuclei image.
Figure 6:
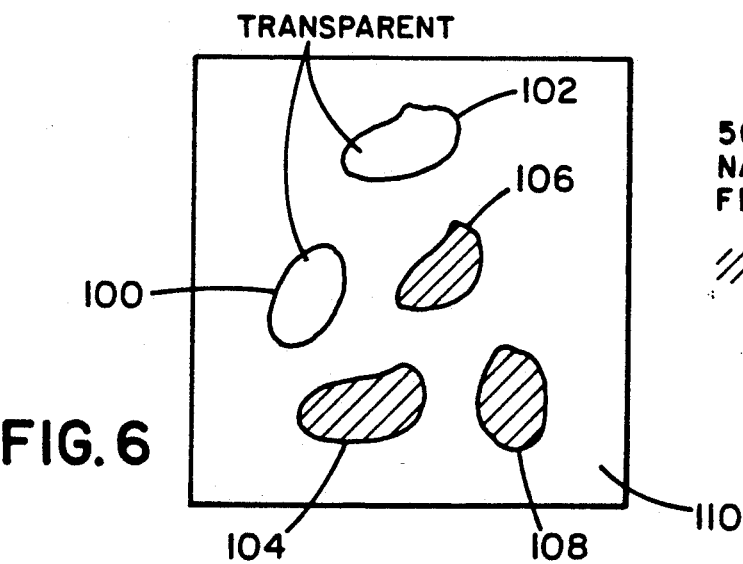
FIG. 6 is a magnified view of the stained cell sample of FIG. 4 as seen through a 500 nanometer narrow band optical filter which yields a proliferation substance image.

The image of FIG. 5 is stored in the internal frame buffer of the image processor 90. The image of FIG. 6 is formed and stored in the internal frame buffer of the image processor 92. It may be appreciated that the pixel values for the images may be sliced using standard image processing techniques to increase the contrast between the cell nuclei and the backgrounds. That is, the areas of high optical density in FIG. 6 such as the cell nuclei 104, 6 and 108 may be shown as being very dense and stored as high optical density pixels, while the background areas 110 may be stored as substantially zero optical density pixels in order to provide a clear threshold or difference between the two areas. This is particularly helpful when performing computations to determine the proliferation index, since the system can differentiate more easily between background and nuclei to be measured.

Figure 8:
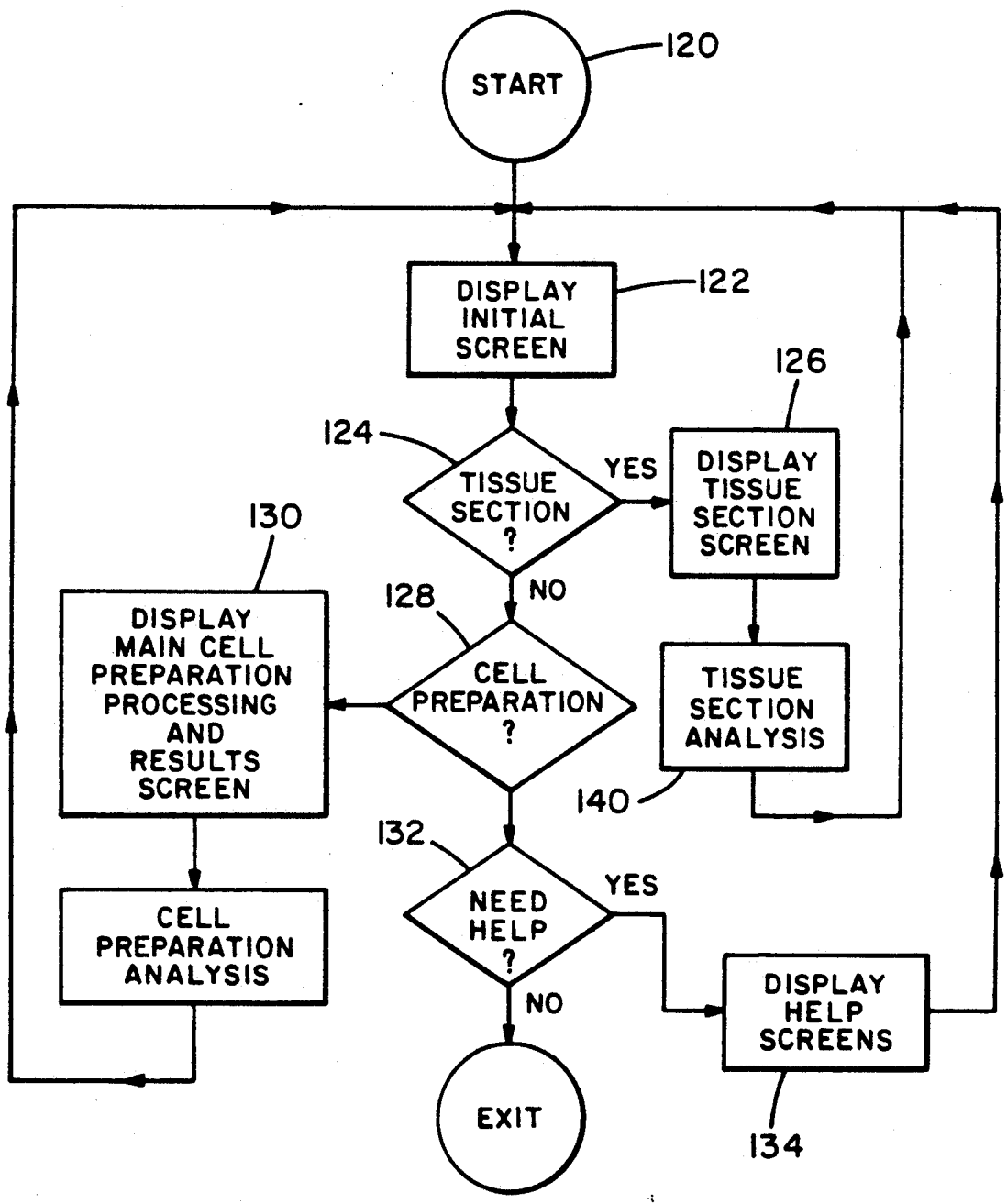
FIG. 8 is a flow chart of a sequence of steps performed by the apparatus of FIG. 1 in selecting a cell sample analysis mode.

Once the images have thus been acquired by the system, the user, as may best be seen in FIG. 8, is interrogated as to whether the images are from a tissue section or a cell preparation. More particularly, in a starting step 120, the system 10 next displays an initial display screen 122 on the instruction monitor 52 and thereby interrogates the user in a step 124 as to whether a tissue section forms the basis for the image being processed. If the user provides a positive response to the system, control is transferred to a step 126 wherein a tissue section screen is displayed on the instruction monitor 52. If the response is negative, control is transferred to a step 128 where the user is questioned as to whether the cell sample is from a cell preparation. If the response is positive, control is transferred to a step 130 wherein a cell preparation processing and result screen of the type shown in FIG. 12 is displayed on the instruction monitor 52. In the event that neither of the selections is made, a step 132 is executed transferring control to a HELP screen 134.

Referring now back to the step 126, it may be appreciated that the screen of FIG. 11 is displayed in the step 126. The screen provides a menu of functions at the right-hand side which are of the type well known to users of automated cell analysis equipment. In particular, the user may select a nuclear threshold function wherein the user may specify the optical density or pixel value at which the system determines for purposes of computation that a particular pixel value is indicative of the presence of a portion of a cell nucleus at that point. Furthermore, an antibody threshold may similarly be set wherein the optical density of the image of FIG. 6 is measured and a threshold is set indicative of the presence or absence of antibody at a particular pixel address. In addition, the user, once having set the thresholds, may then instruct the system to display outlines or shaded areas, also known as masks, of the cell nuclei and the antibodies in a display nuc-anti masking function. Each of the masks is associated with the particular cell nucleus by tag information stored in the system. Once the masking step is finished, control is transferred to a tissue section analysis step 140 which may be seen in more detail in FIG. 9.

Figure 9:
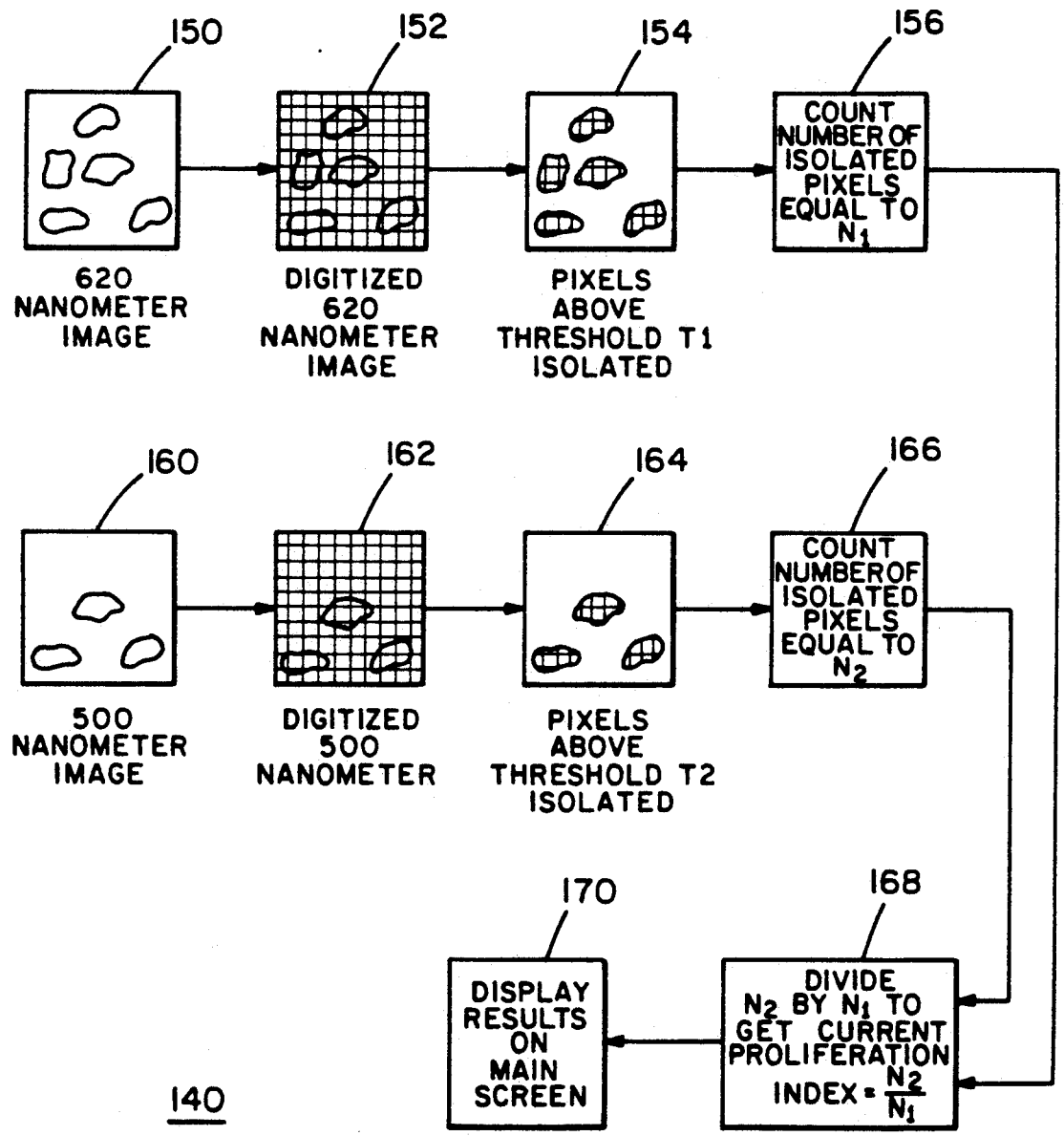
FIG. 9 is a flow chart of a sequence of steps performed by the apparatus of FIG. 1 in determining the proliferation index of a tissue section cell sample.

In FIG. 9, the 620 nanometer image of the type shown in FIG. 5 is received by the camera in a step 150. The image is digitized in a step 152 and a nuclear threshold value T1 for pixels indicating the presence of the cell nuclei is selected in a step 154. Once the threshold has been selected, pixels having a value less than the threshold are reduced to zero leaving a high contrast pixel array for further processing. The pixel array is transferred to the computer system 32 where the number of pixels having values exceeding the selected nuclear threshold value is counted to provide a cell nuclei amount or count N1 in a step 156, which will be used as a proliferation index denominator in later processing.

Similarly, the image of the type shown in FIG. 6 is received by the camera 26 in a step 160. The image is digitized by the image processor 92 in a step 162. An antibody threshold T2 which has been selected by the user reduces the background of the image to zero and effectively isolates the pixels representative of antibody in a step 164. The isolated pixels, that is those pixels having a value greater than the preselected antibody threshold, are then counted by the system 32 and a pixel count number N2 is provided in the step 166.

Thus, it may be appreciated that steps 150 through 156 effectively measure the area of the image field of FIG. 5 wherein cell nuclei are found. The steps 160 through 166 effectively measure the area of the proliferation substance in the image field of FIG. 6. The system 32 in a step 168 then divides the area of the antibody by the area of the cell nuclei and generates a quotient which is equal to the proliferation index. The proliferation index is then displayed on the tissue section screen as a percentage number. In addition, the total nuclear area as computed in steps 150 through 156 is also displayed.

Figure 10:
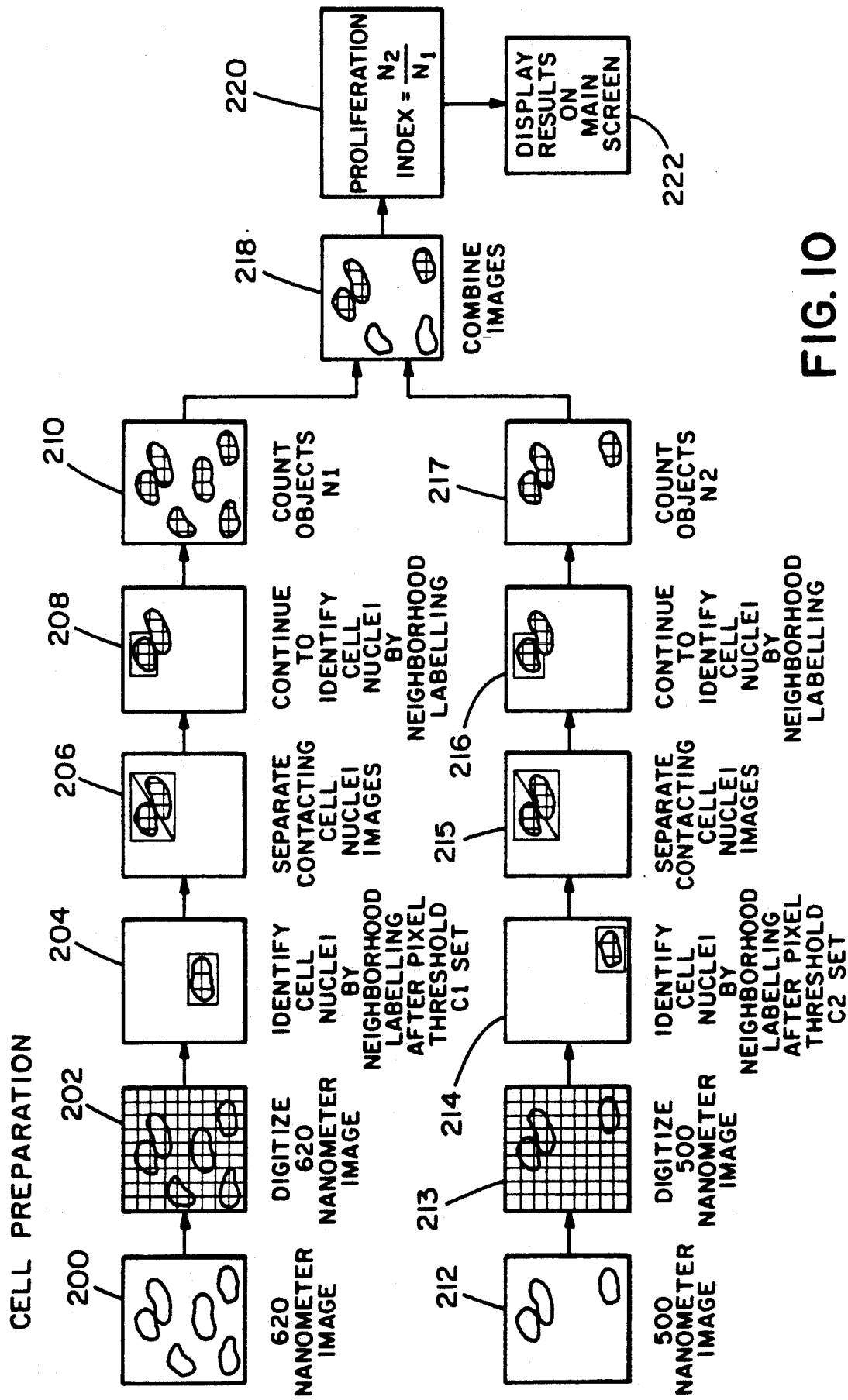
FIG. 10 is a flow chart of the steps carried by the apparatus in determining the proliferation index of a cell preparation cell sample.

In the event that the user has indicated to the system in the step 128 that a cell preparation is being analyzed, control is transferred to step 130 which may be seen in more detail, as shown in FIG. 10. In a step 200, the cell nuclei image of FIG. 5 is received by the camera 20. The cell nuclei image is digitized in a step 202. The digitized image is then analyzed in a step 204 to determine, using neighborhood labelling, what objects are to be considered to be cell nuclei and what objects are not. The objects to be considered to be cell nuclei are indicated by being surrounded by boxes as displayed on the image monitor 30. In a step 206, if two or more of the objects are in contact with each other, the operator is given the opportunity to have the system draw a line of demarcation between them or to manually separate the images himself. The labelling and separating are repeated in a step 208 until all cell nuclei are identified. In a step 210, a threshold value C1 is then applied to the pixel arrays to isolate the pixels, as was done in steps 154 and 164 previously.

Similarly, in a step 212, the proliferation substance image of FIG. 6 is received by the camera 26. The proliferation substance image is digitized in a step 213 and the cell nuclei having more than a threshold number of pixels are identified by neighborhood labelling techniques as cell nuclei containing proliferation substance in a step 214. If any cell nuclei images are touching they are separated in step 215. Next, the remaining cell nuclei are also identified in a step 216. The number of cell objects is counted in a step 217 to yield a nuclear count N2. The images are combined in a step 218 and displayed on the image monitor 30. The number of proliferation substance nuclei N2 is then divided by the number of cell nuclei N1 in a step 220 to produce a proliferation index for the cell preparation sample. The proliferation index is then displayed in a step 222 on the cell preparation screen of FIG. 12.

It may thus be appreciated that the tissue section feature of FIG. 9 allows the proliferation index for a tissue section sample to be easily and rapidly computed using stereological principles which are standard in the field of microscopy. When tissue sections are not used and stereological principles do not apply, the cells may be counted by using the cell preparation technique.

Furthermore, the system provides considerable amplification for determination of the proliferation index. The initial amplification takes place when the proliferation substance is identified with the chromogen and the cell nuclei are stained with the counterstain. A second amplification takes place when the cell nuclei and proliferation substance images are formed by filtering the light through the filters 18 and 24. Further amplification takes place when the threshold values for the antibody and the cell nuclei are set providing high contrast images and high gain digital arrays for further processing.

While there has been illustrated and described a particular embodiment of the present invention, it will be appreciated that numerous changes and modifications will occur to those skilled in the art, and it is intended in the appended claims to cover all of those changes and modifications which fall within the true spirit and scope of the present invention.

What is claimed is:

1. An apparatus for determining a proliferation index of a cell sample, comprising:
   first means for optically sensing portions of a cell sample having a proliferation optically enhanced substance thereon and producing a proliferation substance signal corresponding thereto wherein the first means further comprises an image enhancing optical filter allowing transmission of light for an optical absorbing region of a chromogen associated with the optically-enhanced proliferation substance at a reduced optical absorbing transmission region of a stain optically marking the cell nuclei;
   second means for optically sensing portions of a cell sample having optically marked cell nuclei and producing a cell nuclei signal corresponding thereto wherein the second means further comprises an optical filter allowing transmission of light at an optical absorbing region of a stain, which is optically marking the cell nuclei, and at an optical absorbing region of a chromogen associated with the optically-enhanced proliferation substance;
   first determining means coupled to the first sensing means for determining an amount of the proliferation substance and producing a proliferation substance amount signal corresponding thereto;
   second determining means coupled to the second sensing means for determining an amount of optically marked cell nuclei and producing a cell nuclei amount signal corresponding thereto; and
   proliferation index determining means coupled to the first determining means and receiving the proliferation substance amount signal and coupled to the second determining means and receiving the cell nuclei amount signal therefrom, for determining a proliferation index from the proliferation substance amount signal and the cell nuclei amount signal.

2. An apparatus for determining a proliferation index of a cell sample as defined in claim 1, wherein the first means further comprises an image enhancing optical filter which allows transmission of light at an optical absorbing region of a chromogen associated with the proliferation substance and at an essentially one hundred percent optical transmission region of a stain optically marking the cell nuclei.

3. An apparatus for determining a proliferation index of a cell sample as defined in claim 2, wherein the first means further comprises means for storing a digitized image of the optically-enhanced proliferatino substance.

4. An apparatus for determining a proliferation index of a cell sample as defined in claim 1, wherein the first determining means further comprises means for determining an image area occupied by the optically-enhanced proliferation substance and wherein the proliferation substance amount signal is indicative of the image area occupied by the optically-enhanced proliferation substance.

5. An apparatus for determining a proliferation index of a cell sample as defined in claim 4, wherein the second determining means further comprises means for determining an image area occupied by the optically marked cell nuclei and the cell nuclei amount signal is indicative of the image area occupied by the optically marked cell nuclei.

6. An apparatus for determining a proliferation index of a cell sample as defined in claim 1, wherein the first determining means further comprises means for determining a number of cell nuclei in an image field having the optically-enhanced proliferation substance therein, and the proliferation substance amount signal is indicative of the number of optically marked cell nuclei having the optically-enhanced proliferation substance.

7. An apparatus for determining a proliferation index of a cell sample as defined in claim 6, wherein the second determining means further comprises means for determining a number of optically marked cell nuclei in the image field, and the cell nuclei amount signal is indicative of the optically marked cell nuclei in the image field.

* * * * *